US010342421B2

(12) United States Patent
Plotkin

(10) Patent No.: US 10,342,421 B2
(45) Date of Patent: Jul. 9, 2019

(54) METHOD FOR MEASURING VISUAL ACUITY

(71) Applicant: Boris Plotkin, Rehovot (IL)

(72) Inventor: Boris Plotkin, Rehovot (IL)

(*) Notice: Subject to any disclaimer, the term of this patent is extended or adjusted under 35 U.S.C. 154(b) by 509 days.

(21) Appl. No.: 14/893,133

(22) PCT Filed: May 22, 2014

(86) PCT No.: PCT/IL2014/050456
§ 371 (c)(1),
(2) Date: Nov. 23, 2015

(87) PCT Pub. No.: WO2014/191986
PCT Pub. Date: Dec. 4, 2014

(65) Prior Publication Data
US 2016/0089018 A1    Mar. 31, 2016

(30) Foreign Application Priority Data
May 30, 2013 (IL) .......................... 226678

(51) Int. Cl.
*A61B 3/032*    (2006.01)
*A61B 3/00*    (2006.01)

(52) U.S. Cl.
CPC ............ *A61B 3/032* (2013.01); *A61B 3/0025* (2013.01); *A61B 3/0033* (2013.01); *A61B 3/0041* (2013.01); *A61B 2560/0475* (2013.01)

(58) Field of Classification Search
CPC ................................ A61B 3/032; A61B 3/028
See application file for complete search history.

(56) References Cited

U.S. PATENT DOCUMENTS

| 4,239,351 A | 12/1980 | Williams et al. |
| 5,825,460 A | 10/1998 | Kohayakawa |
| 2011/0116047 A1 | 5/2011 | Polat |

FOREIGN PATENT DOCUMENTS

| WO | 2004089199 A1 | 10/2004 |
| WO | 2007056796 A1 | 5/2007 |

OTHER PUBLICATIONS

International Search Report from a counterpart foreign application—PCT/IL2014/050456, dated Sep. 18, 2014, three pages.

(Continued)

*Primary Examiner* — Daniel L Cerioni
*Assistant Examiner* — Yasmeen S Warsi
(74) *Attorney, Agent, or Firm* — Roach Brown McCarthy & Gruber, P.C.; Kevin D. McCarthy

(57) ABSTRACT

The invention is a system and method for measuring visual acuity. The system comprises a computer or projector adapted to project a computer generated image of an optotype on a surface, e.g. a computer display screen or a screen on a wall, and a control unit. The computer or projector is adapted to project the optotypes with a steadily changing size as a continuum of images. The testing is carried out by changing the optotype size in both directions in order to compensate for the reaction time of the patient. For example, starting with a large optotype, the size is steadily decreased until the patient signals that he can no longer read the optotype. The test then continues starting from a small optotype and steadily increasing the size until the patient signals that he can read the optotype.

7 Claims, 1 Drawing Sheet

| Time | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| A→a | | | | | | | | | | | | | | | | |

| Size | 0.1 | 0.2 | 0.3 | 0.4 | 0.5 | 0.6 | 0.7 | 0.8 | 0.9 | 1.0 | 1.1 | 1.2 | 1.3 | 1.4 | 1.5 | 1.6 |
|---|---|---|---|---|---|---|---|---|---|---|---|---|---|---|---|---|

|   |   |   |   |   |   |   |   | 4 | 3 | 2 | 1 | 0 |   |   | Time |
|---|---|---|---|---|---|---|---|---|---|---|---|---|---|---|---|
|   |   |   |   |   |   |   |   |   |   |   |   |   |   |   | A←a |

(56) References Cited

OTHER PUBLICATIONS

Written Opinion of the International Searching Authority from a counterpart foreign application—PCT/IL2014/050456, dated Sep. 17, 2014, six pages.

Applicant's response to Written Opinion of the International Searching Authority from a counterpart foreign application—PCT/IL2014/050456, dated Mar. 19, 2015, twenty pages.

International Preliminary Report on Patentability and Notification of Transmittal of International Preliminary Report on Patentability from a counterpart foreign application—PCT/IL2014/050456, dated Oct. 8, 2015, sixteen pages.

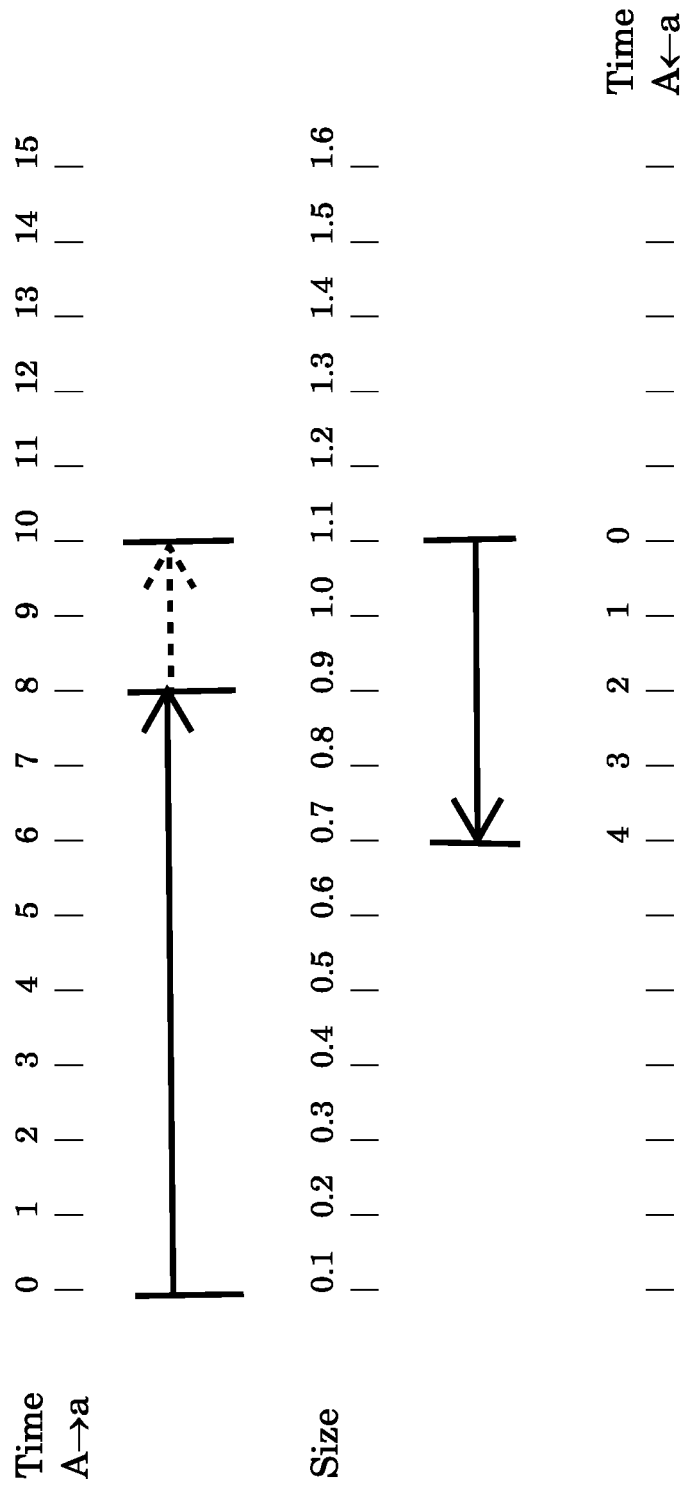

METHOD FOR MEASURING VISUAL ACUITY

FIELD OF THE INVENTION

The invention is from the field of visual sciences. Specifically the invention is from the fields of ophthalmology and optometry. More specifically the invention is from the field of testing human vision.

BACKGROUND OF THE INVENTION

Visual acuity is tested by presenting to client, i.e. the person who is being tested, sets of symbols of various sizes, i.e. optotypes, at a standard distance that approximates infinity in the way that the eye attempts to perceive objects and having the client indicate the smallest optotype that she/he can identify.

The need for standardized vision tests was recognized in the mid eighteen hundreds and shortly thereafter, in 1862, Hermann Snellen developed his well-known and probably the most used of all the eye charts that have been proposed since that time. The optotypes on the Snellen chart are letters that are arranged in a series of rows. The optotypes in each row are of the same size and they are arranged on the page such that, at the standard distance of six meters, the visual angle subtended by the distance between the horizontal and verticals elements that make up each letter is one arc minute and the visual angle subtended by the optotype is five arc minutes. The chart is arranged such that the angle between elements in the letters in successively higher rows increases.

Over the years many other types of chart have been developed. The basic principle of the test for visual acuity has remained the same since the time of Snellen with the major differences related to different forms of optotypes developed, for example, for use with children or clients not familiar with Latin letters.

The results (scores) of visual acuity test are normally recorded as the ratio of the distance between the client's eye and the optotypes divided by the distance at which the smallest optotypes that can be identified by the client could be seen by a person with "standard" vision. Thus a score of 6/6 means that the client can identify an optotype at 6 meters that the standard person can identify at 6 meters, i.e. the client has standard visual acuity. A score of 6/60 means that the client can identify at 6 meters what person having standard visual acuity can identify at 60 meters, i.e. the client has very poor visual acuity, and a score of 6/4 means that the client has much better visual acuity than the standard person.

Many different methods of displaying the optotypes to the client have been developed over the years. The most common method is by means of a chart comprised of rows of optotypes printed in black on a white background that is hung on a wall. Another common method is to print the optotypes on a transparent substrate that is backlighted to improve contrast. In other methods the entire chart or individual optotypes are reproduced on slides that are optically projected on a wall or screen the required distance from the client. Much more sophisticated display methods are described, for example in U.S. Pat. No. 4,239,351 and US 2011/0116047.

U.S. Pat. No. 4,239,351 describes an apparatus for testing visual acuity based on two electro-optic display devices to be viewed by a patient and an examiner respectively. Typically the apparatus is used for testing by presenting a single optotype to the patient at a size below which he is able to identify it and then rapidly zooming the optotype to a larger size until the patient can identify it. The examiner then sequentially presents rows of optotypes of increasingly smaller size until the patient can identify all of them. According to the method in this patent the zoom function is used only to find an approximate starting point for carrying out the visual acuity test using a row by row presentation of the optotypes.

US 2011/0116047 describes a method of visual evaluation or training based on an apparatus that displays symbols on a display device and electronically and optically changes the parameters, including the size, of the symbols displayed. The display device is a hand held device and the evaluation or training session is controlled and results recorded either by software installed on the hand held device or remotely on a server connected to the hand held device via the Internet or a cellular phone network. Also described is a "staircase" method of testing visual acuity in which the display and client are much closer together than in the usual methods. In this case the display device can be stationary, e.g. a desktop computer screen, or a handheld device. The client is required to respond to a displayed series of symbols in which the physical size of the symbols is sequentially reduced in a step-like fashion. The response of the client can be oral or by activating an input device such as a keyboard. The response depends on the nature of the symbol and can be, for example, the name of a letter or, the shape or orientation. When the client can no longer correctly identify the symbol displayed on the screen the system can automatically calculate a score for the test.

Because of the sequential manner in which the optotypes are displayed or read from the charts methods of testing for visual acuity are relatively time consuming. The results are very subjective since they are dependent on the responses and in some cases the reaction time of the client. In some cases the results are influenced by guesswork or by memorization from previous exposure to the symbols and or the sequence in which they are displayed.

One way to reduce these effects and to increase the accuracy of the results is to repeat the test one or more times but this increases the required time.

It is a purpose of the present invention to provide a method for testing the visual acuity of a person that minimizes the drawbacks of the prior art.

Further purposes and advantages of this invention will appear as the description proceeds.

SUMMARY OF THE INVENTION

In a first aspect the invention is a method for measuring visual acuity of a client. The method comprises three steps:
A. in a first step:
  a. activating a projector comprising a zoom lens to project a single large computer generated optotype having a size that the client will surely be able to identify on an appropriate surface a known distance from the eyes of the client;
  b. activating the zoom lens to smoothly reduce the size of the optotype;
  c. activating a clock to measure the time from the time when the zoom lens is activated;
  d. receiving at a control system a signal from the client indicating that she/he can no longer identify the optotype;

e. recording in a data storage unit of a control system, the elapsed time from the start of the activation of the zoom lens until the signal from the client is received at the control system;
f. stopping the action of the zoom lens several seconds after the signal is received from the client;
g. recording in the data storage unit, the elapsed time from the start of the activation of the zoom lens until the action of the zoom lens is stopped;

B. in a second step:
a. activating the zoom lens to smoothly increase the size of the optotype from the size of the optotype that was projected on the surface in step A.d.:
b. activating the clock to measure the time from the time when the zoom lens is activated in step B.a.;
c. receiving at a control system a signal from the client indicating that the size of the optotype has been enlarged until she/he can now identify the optotype;
d. stopping the action of the zoom lens when the signal is received from the client;
e. recording in the data storage unit, the elapsed time from the start of the activation of the zoom lens in step B.a. until the signal is received from the client;

C. in a third step:
a. determining the optotype sizes corresponding to the elapsed times recorded in steps A.e., A.g., and B.e.; and
b. determining the true threshold value of the minimal size of the optotype that can be identified by the patient, wherein the true threshold value is the visual acuity of the patient.

The method of the invention is characterized in that in the first and second steps the optotypes are projected with a steadily changing size as a continuum of images and following step A.a. all steps of the method are carried out automatically by components of the control system.

In embodiments of the method of the invention in the first step the size of the projected optotype is enlarged from a size that client will surely not be able to identify and in the second step the size of the projected optotype is decreased.

In embodiments of the method of the invention in the third step the reaction time of the client is determined by components of the control system.

In embodiments of the method of the invention the optotype used in the first step is different from the optotype used in the second step.

In embodiments of the method of the invention at least some of the determinations in step C.a. are carried out during execution of the first and the second steps.

In embodiments of the method of the invention all steps of the method are completed in no more than one minute.

In a second aspect the invention is a system for carrying out the method of the first aspect. The system comprises:
a. a projector comprising a zoom lens; and
b. a control system.

The system of the invention is characterized in that the projector and the control system are adapted to project computer generated optotypes with a steadily changing size as a continuum of images and the control system is adapted to automatically carry out all steps of the method.

In embodiments of the system of the invention the control system comprises: a processor, software, data storage unit, internal clock, input means, and a display screen.

In embodiments of the system of the invention the system additionally comprises a system for detecting preferential looking or fixation of the client's eyes.

All the above and other characteristics and advantages of the invention will be further understood through the following illustrative and non-limitative description of embodiments thereof, with reference to the appended drawings.

BRIEF DESCRIPTION OF THE DRAWINGS

FIG. 1 schematically illustrates the method of the invention.

DETAILED DESCRIPTION OF EMBODIMENTS OF THE INVENTION

The invention is a system and method for measuring visual acuity. The system comprises standard non-medical apparatus in order to carry out a medical examination. It comprises a computer or a projector adapted to project a computer generated image of an optotype on a surface, e.g. a computer display screen or a screen on a wall at any fixed distance, e.g. four to six meters, from the eyes of the client and a control unit.

The projector comprises a zoom lens that enables continuous digital or optical zoom in the range of 20×. The projector is adapted to allow the operator to select the rate at which the zoom will automatically change in either a linear or logarithmic manner. The direction of the change of the zoom can be from the largest size of the optotype to the smallest or vice versa. The optotypes are constructed according to Snellen standards and can be in any form, e.g. numerals or letters in any language or symbols. However since the Hindu-Arabic numerals (0, 1, 2, 3, 4, 5, 6, 7, 8, 9) are familiar to almost every person in the world as evidenced by their appearance on the bank notes of most countries, their use as optotypes are suggested.

It is also noted that the optotypes can also be displayed to the client using a computer and computer, television, or similar display screen as long as the computer is programmed to continuously vary the size of the optotype at a known rate and not to display a series of optotypes with different sizes in a "staircase" manner.

Herein, including in the claims, references to projectors and zoom lenses are to be understood to include—and can be replaced by all methods of and equipment capable of producing and displaying optotypes with continuously changing sizes.

The system of the invention includes a control unit. The control unit comprises a processor, software, data storage unit, internal clock, input means, and a display screen. The software is adapted to determine the visual acuity and reaction time of the client as will be described herein below. In embodiments of the invention the control unit can be a PC or laptop computer or a handheld device such as a smart phone comprising an application dedicated to carrying out the method of the invention. The input means can be any of the devices known in the art, e.g. a keyboard, a keypad, a computer mouse, voice recognition, or a camera with image processing software adapted to identify hand signals or eye movement.

The operator uses his input means to enter information such as the date and time; his identity; the name, age, sex, and identity number of the client; and possibly information about the medical history or condition of the client into the data storage unit of the control unit. He then initiates the test by entering a code or other way to identify the type of optotype to be used, e.g. Latin letter, numbers, the letter "E" in various orientations, and the rate at which the zoom feature of the projector changes the size of the projected optotype. Following initiation by the operator, the processor and software control the entire test from start to finish, including recording the measurements and analyzing them to determine the result. It is noted that in embodiments of the invention the type of optotype to be displayed is determined by the software and processor either randomly or using some criterion such as the previously stored information about the client.

The client uses her/his input means to signal that she/he can no longer identify the optotype (for decreasing size) or can first identify it (for increasing size). Depending on the type of input means available the client can communicate to the control system, for example, by uttering a word, e.g. "stop, hand signal, e.g. thumbs up, or pressing on a predetermined key on a keyboard or touch pad, or by pressing on a bell. Embodiments of the system of the invention include a system for detecting preferential looking or fixation of the client's eyes.

The measurement of visual acuity is carried out by projecting a single large optotype having a size that the client will surely be able to identify (or alternatively one that is too small to identify) on an appropriate surface, e.g. a screen or wall, a known distance, e.g. 4-6 meters using a projector with a zoom lens or at any distance using a computer and computer display screen, from the client's eyes. As the image appears on the screen the zoom is activated to smoothly reduce (or increase) the size of the optotype and a clock is activated to measure the elapsed time from the start of a "run" until the client signals that he can no longer identify the optotype. The elapsed time from the start of the run until the signal from the client is received by the control unit is recorded in the data storage unit. Since the rate of the zoom, i.e. the change in optotype size per second, is known, the algorithms in the software can relate the elapsed time to the size of the optotype at the end of the run. The fact that the progress of the test doesn't have to be halted at frequent intervals to enable the operator to verify that the client has correctly identified the optotypes by asking the client to read them out loud after each optotype or group of optotypes is displayed as is customarily done in the prior art is one of the main advantages of the present invention, i.e. the test can be completed in a fraction of the time required for a conventional test.

The method as described in the previous paragraph will not be accurate because of the reaction time of the client. As a result of the reaction time, by the time the client's "stop" signal is received by the processor, the corresponding size of the optotype will be smaller than the true threshold value. Therefore the method of the invention requires a second step to correct for this error.

In preparation for the second step the control system does not stop the zoom on the signal from the client indicating that she/he can no longer identify the optotype but continues in the same direction for several, e.g. two or three, more seconds. For the second step the zoom direction is then reversed, the clock is restarted and the optotype size is increased from an initial size which is too small for her/him to identify until the client signals that she/he can identify the optotype. Also when the optotype size changes in this direction, the result is affected by the reaction time. The reaction time is one half of the time interval between the times that the client stopped the clock going in both directions.

Reaction time has two components: a sensory component related to the time it takes for the eye to see, the brain to process what is seen and the nervous system to notify the appropriate organ to take action and a motor component related to the time that is used to carry out the action, e.g. the time required for a finger to press a key on the keyboard to indicate that the optotype can no longer be seen. In order to insure that the true threshold is constant in both steps, the optotype projected is not changed (except for size) in the entire first step and the entire second step of the method. Two different optotypes can be used in the test—one in each step—if they have what is known in the art as the same visible legibility. For example, the ten Hindu-Arabic numerals are divided into three groups: (5, 6, 8, 9), (1, 4, 7), and (2, 3, 0); wherein the visual legibility of the optotypes in each group is the same and each group has a different visual legibility. Thus, for example, numeral 5 could be used as the optotype in the first step and numeral 8 in the second step.

FIG. 1 schematically illustrates the method of the invention by describing an example in which the rate of zoom is set to change, i.e. increase or decrease, the size of the projected optotype at the constant rate of one optotype size per second.

The middle scale represents the optotype size as a ratio of the distance between the eyes of the client and the surface on which the optotype is displayed to the distance at which a person having "standard" vision could identify the same size optotype. The sizes are represented in equal steps ranging from the largest on the left to the smallest on the right. Thus for example a size of 0.1 means that if the client can identify an optotype of that size at 6 meters then a person with standard vision can identify the same optotype at 60 meters, or if the client can identify an optotype of that size at 4 meters then a person with standard vision can identify the optotype at 40 meters, etc. The range shown in FIG. 1 is suitable for testing clients having visual acuity that is characteristic of the majority of humans but embodiments of the software in the processor enable the range to be extended in either direction for special cases of clients having extremely good or bad visual acuity if necessary.

The top and bottom scales represent time measured by an internal clock in seconds for the change in size of the displayed optotype for the direction of zoom from larger optotype to smaller in the top scale and from smaller optotype to larger in the bottom scale. The distance between two adjacent marks on these scales, i.e. one second in this example, represents the time required for a one-step change in the size of the optotype.

The horizontal arrow located between the A→a time scale and the size scale schematically shows the first step of the method of the invention. The test initiates by displaying the largest optotype at time zero corresponding to an optotype size of 0.1 and the zoom steadily decreases the size of the optotype until the clock is stopped at eight seconds by the client signaling to the control unit, that he can no longer identify the optotype, e.g. by pressing on the letter "s" on a computer keyboard in the data storage unit. The processor determines the size of optotype, i.e. 0.9 that corresponds to the time of eight seconds and records the elapsed time and optotype size in the data storage unit of the control system. In preparation for step two of the method, the zoom continues to reduce the size of the optotype, e.g. for two more seconds, at which time the zoom is stopped. The elapsed time from the beginning of the run until the zoom is stopped is also recorded and from this elapsed time the processor is able to determine the corresponding optotype size, i.e. 1.1.

The horizontal arrow located between the a→A time scale and the size scale schematically shows the second step of the method of the invention. The zoom is activated to steadily increase the size of the optotype from the size at which it was stopped in the first step, i.e. 1.1. Simultaneously the clock is activated to measure time. The clock is stopped by a signal from the client to the control unit, which indicates that she/he can now identify the optotype. It is noted that reaction time may depend on the method used by the client to signal the control unit; therefore the same method of signaling should be used in both steps of the test. The processor records the elapsed time, i.e. 4 seconds, from which the change in the size of the optotype, i.e. 0.4, is determined. The processor then determines the size of the optotype, i.e. 0.7, corresponding to the time at which the signal from the client is received by subtracting 0.4 from the starting size of 1.1.

Assuming that the reaction times were the same in both directions, the true threshold value of the size of the optotype that the client can identify is determined by the processor to be one half of the sum of the results obtained in steps 1 and 2, i.e. (0.9+0.7)/2=0.8.

The reaction time of the client is equal to one half of the time required to change the optotype size from that identified by the client in step 1 to that identified in step 2, i. e. (0.9−0.7)/2=one optotype size=1 second.

The entire test from initiation of step 1 to the final result that is determined and displayed by the control unit will typically take less than one minute, but can take longer, especially if the rate of zoom has to be lowered, for example for an elderly client with very slow reaction time.

The ease and accuracy of the visual acuity tests that are performed according to the method of the invention are of great importance to the health care personnel that perform the tests and to their clients. The speed with which the testing of visual acuity can be carried out using the method of the invention is of great financial significance to organizations that have to pay for large numbers of these tests such as hospitals, health maintenance organizations, and the military. Additionally both the ease and speed with which the examinations can be carried out combined with the use of non-specialized and therefore not expensive equipment offers the ability of mass testing of individuals presently untested such as school age children in developed and in underdeveloped countries.

The key to the method is the mechanism that changes the zoom, which is adapted to project the optotypes with a steadily changing size as a continuum of images. This is as opposed to the prior art which displays the optotypes in a step-like fashion, i.e. projects optotypes of predetermined size one after the other. It is emphasized that in the example shown in FIG. 1 and described above the rate of zoom was adjusted so that elapsed time of one second exactly corresponded to the change of one optotype size for simplicity in order to illustrate the invention; however the processor of the system is able to carry out the method using a wide range of zoom speeds.

Embodiments of the invention are adapted to determine results for the visual acuity with varying degrees of precision by employing methods such as: allowing the operator to determine the speed of zoom; repeating the test one or more additional times; using adaptive protocols that take into account the result of a previous test as the starting point for a follow up test—either at the same or a subsequent session, and employing more sophisticated statistical methods to determine the visual acuity from the measured results. In one embodiment, the software is adapted to compare the measured reaction time of the client to average reaction times for individuals fitting a similar profile, e.g. same age group, sex, or medical condition, and if statistically significant differences occur will either recommend to the operator that the test should be rerun or automatically cause the processor to rerun the test one or more times.

Although embodiments of the invention have been described by way of illustration, it will be understood that the invention may be carried out with many variations, modifications, and adaptations, without exceeding the scope of the claims.

The invention claimed is:

1. A system for making a measurement of the visual acuity of a client that has been corrected for the client's reaction time, the system comprising:
   a) a control unit comprising: a computer or processor, software, a data storage unit, an internal clock, and input means;
   b) a projector comprising a zoom lens; and
   c) a surface at a known distance from the eyes of said client;
   wherein the control unit is configured to execute the following sequence of steps:
      i) activate the computer to generate a single optotype;
      ii) activate the projector to project the single computer generated optotype on the surface with a size that the client will surely be able to identify;
      iii) activate the zoom lens to smoothly reduce the size of the optotype as a continuum of images and to simultaneously activate the clock;
      iv) receive a signal from the input means indicating that size of the optotype has been reduces until the client can no longer change the perception from one optotype to another;
      v) record in the data storage unit the elapsed time from the start of the activation of the zoom lens until the signal is received;
      vi) stop the action of the zoom lens several seconds after the signal is received;
      vii) record in the data storage unit the elapsed time from the start of the activation of the zoom lens until the action of the zoom lens is stopped;
      viii) activate the zoom lens to smoothly increase the size of the optotype as a continuum of images from the size that was projected on the surface in step vi and simultaneously activate the clock;
      ix) receive a signal from the input means indicating that size of the optotype has been increased until the client can identify the optotype;
      x) stop the action of the zoom lens when the signal is received in step ix;
      xi) record in the data storage unit the elapsed time from the start of the activation of the zoom lens in step viii until the signal is received in step ix;
      xii) activate the computer or processor to determine the optotype sizes corresponding to the elapsed times recorded in steps v, vii, and xi; and
      xiii) activate the computer or processor to determine from the three optotype sizes determined in step xii the true threshold value of the minimal size of the optotype that can be identified by the client; wherein the true threshold value is the visual acuity of the client that has been corrected for the client's reaction time.

2. The system of claim 1, wherein the projector and surface are replaced by a display screen and a computer programmed to continuously vary the size of the optotype at a known rate.

3. The system of claim 1, wherein the control unit is one of: a personal computer (PC), a laptop computer, and a handheld device.

4. The system of claim 3, wherein the handheld device is a smart phone.

5. The system of claim 1, wherein the input means is one of: a keyboard, a keypad, a computer mouse, voice recognition, or a camera with image processing software adapted to identify hand signals or eye movement.

6. The system of claim 1, wherein in steps ii to iv the projector is activated to project the single computer generated optotype on the surface or display with a size that the client will surely not be able to identify to a size that the client can identify and in steps vii and ix the projector is activated to project the single computer generated optotype on the surface or display until it is large enough for the client to be able to identify.

7. The system of claim 1, wherein the optotype used in steps ii to vii is different from the optotype used in steps viii to xi.

* * * * *